(12) United States Patent
Axelrod et al.

(10) Patent No.: US 9,441,260 B2
(45) Date of Patent: *Sep. 13, 2016

(54) METHOD AND SYSTEM FOR REAL-TIME, NON-INVASIVE MONITORING OF A BIOLOGICAL MATERIAL IN A SEALED CONTAINER

(71) Applicant: PHYSICAL LOGIC AG, Zurich (CH)

(72) Inventors: Noel Axelrod, Jerusalem (IL); David Nuttman, Ness Ziona (IL); Moria Shimoni, Petah Tikva (IL)

(73) Assignee: VAYU SENSE AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,034

(22) Filed: Nov. 11, 2012

(65) Prior Publication Data

US 2013/0337492 A1 Dec. 19, 2013

Related U.S. Application Data

(60) Provisional application No. 61/660,744, filed on Jun. 17, 2012.

(51) Int. Cl.
| | |
|---|---|
| *C12Q 1/04* | (2006.01) |
| *G01N 21/35* | (2014.01) |
| *G01N 21/39* | (2006.01) |
| *G01N 33/497* | (2006.01) |
| *C12Q 1/00* | (2006.01) |
| *G01N 33/02* | (2006.01) |
| *G01N 33/49* | (2006.01) |
| *C12M 1/34* | (2006.01) |
| *G01N 21/3504* | (2014.01) |

(52) U.S. Cl.
CPC ............. *C12Q 1/04* (2013.01); *C12M 41/34* (2013.01); *C12M 41/46* (2013.01); *C12Q 1/00* (2013.01); *G01N 21/35* (2013.01); *G01N 21/39* (2013.01); *G01N 33/497* (2013.01); *G01N 21/3504* (2013.01); *G01N 33/02* (2013.01); *G01N 33/49* (2013.01); *G01N 2033/4977* (2013.01)

(58) Field of Classification Search
None
See application file for complete search history.

(56) References Cited

U.S. PATENT DOCUMENTS

| 4,889,992 A | 12/1989 | Hoberman |
| 5,155,019 A | 10/1992 | Sussman |
| 5,482,842 A | 1/1996 | Berndt |
| 6,955,652 B1 * | 10/2005 | Baum et al. ................ 600/532 |
| 7,427,501 B2 * | 9/2008 | Bachur et al. ............ 435/287.3 |
| 2011/0275112 A1 * | 11/2011 | Sarver et al. ................. 435/34 |

FOREIGN PATENT DOCUMENTS

| EP | 1724335 A1 | 11/2006 |
| WO | 2006047336 A2 | 5/2006 |
| WO | 2008053507 A2 | 5/2008 |
| WO | 2012001633 A2 | 1/2012 |

OTHER PUBLICATIONS

Arpi et al., A Novel Screening method for the detection of microbial contamination of platelet concentrates, Vox Sang, 1993, 65:335-336.*
Snyder et al., Extended storage of platelets in a new plastic container, Transfusion, 1985, vol. 25, No. 3.*
CBS Report, Canadian Blood Services, 2010.*
Weidmann et al., Carbon isotopomers measurement using mid-IR tunable laser sources, Isotopes in Environmental and Health Studies, vol. 41, No. 4, Dec. 2005.*
Weidmann et al., Development of a compact quantum cascade laser spectrometer for field measurements of CO2 isotopes, Applied Physics, B 80, 255-260, 2005.*
Dhimitri et al., Infrared Analysis of Yeast Headspace Gases, Canadian Light Source, Activity Report, 2009.*
Mazarevica et al., On-Line Fermentation Monitoring of Mid-Infrared Spectroscopy, Applied Spectroscopy, vol. 58, No. 7, 2004.*
Threlkeld, Detection of Microbial Contamination Utilizing an Infrared CO2 Analyzer, Journal of Food Science, vol. 47, 1982.*
Tosi et al., Assessment of In-Line Near Infrared Spectroscopy for Continuous Monitoring of Fermentation Processes, Biotechnol. Prog. 19, 1816-1821, 2003.*
S. Ribault et al., "Rapid screening method for detection of bacteria in platelet concentrates" Journal of Clinical Microbiology vol. 2 (2004) pp. 1903-1908.
International Search Report for corresponding application PCT/IL2013/050520; Mail date Sep. 18, 2013.

* cited by examiner

*Primary Examiner* — Taeyoon Kim
*Assistant Examiner* — Srikanth Patury
(74) *Attorney, Agent, or Firm* — Cantor Colburn LLP

(57) ABSTRACT

A biological material such as platelets is sealed inside a container with a dead space to accommodate a metabolic gas. The concentration of the gas in the dead space is monitored while the container remains sealed. In some embodiments, the container is permeable to the gas. In other embodiments, the biological material is the only growth medium in the container. The disposal of the biological material is in accordance with the monitored gas concentration. Preferably, the gas concentration is measured spectroscopically. A container for a biological material includes a main body that retains the biological material but that is permeable to a gas and a reservoir in fluid communication with the main body that is transparent to an optical wavelength that is absorbed by the gas.

3 Claims, 5 Drawing Sheets

METHOD AND SYSTEM FOR REAL-TIME, NON-INVASIVE MONITORING OF A BIOLOGICAL MATERIAL IN A SEALED CONTAINER

This is a continuation-in-part of U.S. Provisional Patent Application No. 61/660,744, filed Jun. 17, 2012

FIELD AND BACKGROUND OF THE INVENTION

The present invention relates to the monitoring of a material, such as (but not limited to) a blood component, that can serve, intentionally or unintentionally, as a growth medium for the growth of microorganisms such as bacteria, and that is contained within a sealed container, and, more particularly, to such monitoring in real time and in a non-invasive manner, i.e., without opening the container and withdrawing a portion of the material e.g. for incubation in another growth medium in a separate container. Such materials are called "biological materials" herein.

The primary intended application of the invention is to detecting bacterial contamination of a biological material such as platelets; but the scope of the invention is wider than this primary intended application and is defined by the appended claims.

Platelets are a component of blood that is involved in blood clotting. Blood components such as red blood cells, white blood cells, plasma and platelets, commonly are used for transfusions. Platelet transfusions often are given to patients undergoing procedures such as chemotherapy for leukemia, bone marrow transplants, radiation treatment, organ transplants, and surgeries such as cardiopulmonary bypass, and as therapy for medical conditions including multiple myeloma, aplastic anemia, AIDS, hypersplenism, idiopathic thrombocytopenic purpura and sepsis.

Isolation of platelets for transfusion is effected by one of two methods: isolation from collected units of whole blood units or collection by apheresis.

Allogenic blood for transfusion is a potential source of infection by a variety of known and unknown transmissible agents. Over the last three decades, the risk of transfusion-related transmission of viral diseases such as human immunodeficiency virus (HIV) I/II, hepatitis C virus (HCV), hepatitis B virus (HBV) and human T-lymphotropic virus (HTLV) I/II has decreased dramatically. With blood products now being routinely screened by ultrasensitive techniques to minimize the risk of transmitting viruses to recipients, the known risk of transmission of bacteria has emerged as the greatest residual threat of transfusion-transmitted disease. Bacterial contamination has proved more difficult to address than viral contamination, and remains the most prevalent transfusion-associated infectious risk. This is especially true for platelets, which are stored at room temperature (22° C.) for up to five days (rather than the previous practice of storage for up to seven days), in bags that are permeable to oxygen and carbon dioxide, and under sufficient constant agitation to provide adequate oxygenation, to prevent platelet aggregation and to maintain optimal platelet viability and functional properties. Storage at room temperature provides an environment where any bacteria that are introduced to the blood component during the collection process may proliferate and subsequently cause bacteremia in the patient. The risk of bacterial contamination in platelets is estimated to be one in 1500, which is one to two orders of magnitude greater than the combined risk of viral infections (S. Ribault et al., Rapid screening method for detection of bacteria in platelet concentrates, *Clinical Microbiology* vol. 2 (2004) pp. 1903-1908).

Sussman et al., U.S. Pat. No. 5,155,019, test for the presence of microorganisms in a possibly contaminated substance by transferring some of the substance to a sterile vial that is impermeable to carbon dioxide and that includes a growth medium for the microorganisms, sealing the vial, incubating the vial and using infrared spectroscopy to monitor the concentration of carbon dioxide in the head space above the growth medium in the vial. The vial is positioned between a source of a beam of infrared radiation and a detector of the beam so that the beam traverses the head space.

Berndt, U.S. Pat. No. 5,482,842 teaches a similar method, but uses two sources and two detectors. Bachur et al. EP 1 724 335 A1, teach a similar method that uses one or more tunable lasers as the infrared source(s). Hoberman, U.S. Pat. No. 4,889,992, teaches a vial that is adapted for use in such methods: the vial includes a passive mechanism for keeping liquid and foam from the growth medium out of the path of the infrared beam.

U.S. Pat. No. 5,155,019, U.S. Pat. No. 5,482,842, EP 1 724 335 A1 and U.S. Pat. No. 4,889,992 all are incorporated by reference for all purposes as if fully set forth herein. The methods taught therein are not suitable for monitoring bacterial contamination of platelets because those methods would require transfer of some platelets from a platelet bag to a vial that includes a growth medium, followed by incubation of the vial. Aside from increasing the risk of inadvertent contamination of the remaining platelets, these methods require incubation time and so may be inconsistent with the relatively short shelf life of platelets.

It would be highly advantageous to have an in-situ, real-time, non-invasive method of monitoring platelet bags for bacterial contamination.

SUMMARY OF THE INVENTION

The present invention detects live biological activity in a biological material in its original storage container as is, without need for sample incubation. Therefore, this invention provides means for in situ and real-time monitoring of biological activity in the biological material storage container.

The goal of the detection is to determine the presence of microorganisms, such as bacteria, for the purpose of either detecting microbial contamination or measuring desired bacterial growth in pharmaceutical production applications such as the production of antibodies.

According to the present invention there is provided a method of handling a biological material, including the steps of: (a) introducing the biological material into a container that is permeable to a metabolic gas; (b) subsequent to the introducing of the biological material into the container: sealing the container in a manner that leaves a dead space in the container for accommodating the metabolic gas; and (c) subsequent to the sealing of the container: monitoring a concentration of the metabolic gas in the dead space while the container remains sealed.

According to the present invention there is provided a method of handling a biological material, including the steps of: (a) introducing the biological material into a container; (b) subsequent to the introducing of the biological material into the container: sealing the container in a manner that leaves a dead space in the container for accommodating a metabolic gas; and (c) subsequent to the sealing of the container: monitoring a concentration of the metabolic gas in the dead space while the container remains sealed; wherein a growth medium separate from the biological material is absent from the container at least during and after the introducing of the biological material into the container.

According to the present invention there is provided a system for handling a biological material, including: (a) a sealable container, for the biological material, that is permeable to a metabolic gas; and (b) a mechanism for monitoring a concentration of the metabolic gas in a dead space of the container while the container is sealed with a quantity of the biological material therein that only partly fills the container.

According to the present invention there is provided a container including: (a) a main body that retains biological materials but that is permeable to a gas; and (b) a reservoir, in fluid communication with the main body, that is transparent to an optical wavelength that is absorbed by the gas.

The methods of the present invention are methods of handling a biological material such as food, human or animal tissues, and cell cultures, with particular application to blood components such as platelets. The biological material is introduced into a container. Then the container is sealed in a manner that leaves a dead space in the container for accommodating a metabolic gas. After the container has been sealed, the concentration of the metabolic gas in the dead space is monitored while the container remains sealed.

By "metabolic gas" is meant herein a gas that is produced or consumed in the course of some living organism's metabolism. Examples of gases that are specifically excluded from this definition include helium and argon. Examples of gases that are specifically included in this definition are carbon dioxide, oxygen, ammonia, hydrogen sulfide, methane, ethane, butane, ethylene, sulfur dioxide, carbonyl sulfide and nitric oxide. The description below of the preferred embodiments focuses specifically on carbon dioxide.

The present invention is distinguished from the prior art at least by one or both of the following two features:

1. The container is permeable to the metabolic gas. For example, plastic platelet storage containers are permeable to carbon dioxide and oxygen.

2. The only growth medium, if any, inside the container, after the biological material has been introduced to the container, is the biological material itself. This feature distinguishes the present invention from the conventional method of assaying bacterial contamination of a biological material by adding a sample of the biological material to a separate growth medium and incubating the growth medium.

Preferably, the biological material is disposed of in accordance with the monitored concentration of the metabolic gas. "Disposing" of the biological material means either using the biological material for its intended purpose (because the monitored concentration of the metabolic gas indicates that the biological material is suitable for its intended purpose) or discarding the biological material (because the monitored concentration of the metabolic gas indicates that the biological material should not be used for its intended purpose). Most preferably, the methods include estimating, from the monitored concentration of the metabolic gas, the degree to which the biological material is contaminated by microorganisms.

Preferably, the monitoring is effected by optical spectroscopy, i.e., in the infrared and/or visible portions of the electromagnetic spectrum. Most preferably, the optical spectroscopy includes measuring an intensity of a beam of light that traverses the dead space in the container. The most preferred bands for the optical spectroscopy are in the infrared portion of the electromagnetic spectrum. Also most preferably, the optical spectroscopy includes monitoring of the individual concentrations of two or more isotopologues of the metabolic gas.

Optionally, the dead space is extended for the purpose of the optical spectroscopy, by attaching to the container a reservoir that is transparent to the beam of light. The optical spectroscopy then is effected as the beam of light traverses the reservoir.

In the application of the present invention to monitoring the progress of fermentation, in which the biological material serves as a growth medium for one or more deliberately introduced microorganism species, the methods of the present invention include introducing a population of that/those species to the container, separately from the introduction of the biological material into the container, before the container is sealed. In this application of the present invention, the metabolic gas is a gas that is produced or consumed by the introduced microorganisms.

Preferably, the container is sterilized before the biological material is introduced into the container.

A basic system of the present invention, for handling a biological material, includes a sealable container, for the biological material, that is permeable to a metabolic gas, and a mechanism for monitoring the concentration of the metabolic gas in a dead space of the container while the container is sealed with a quantity of the biological material inside the container that only partially fills the container.

Preferably, the mechanism for monitoring the concentration of the metabolic gas is an optical spectroscopic mechanism. Most preferably, the mechanism includes a source, such as a tunable laser, of a light beam and a mechanism for positioning the container relative to the light source so that the light beam traverses the dead space in the container.

A basic container of the present invention, for containing biological materials, includes a main body that retains the biological materials but that is permeable to a gas such as a metabolic gas as defined above, and a reservoir that is in fluid communication with the main body and that is transparent to an optical (infrared or visible) wavelength that is absorbed by the gas. That the reservoir is in "fluid communication" with the main body means that the gas can flow freely between the main body and the reservoir.

In one class of embodiments, the main body is opaque to the optical wavelength: the main body is insufficiently transparent to the optical wavelength to allow monitoring of gas concentration via measurement of absorption of light of that wavelength. One example of such a container is a barrel, for the aging of wine, to which reservoir 40 of FIG. 3 below has been attached.

BRIEF DESCRIPTION OF THE DRAWINGS

Various embodiments are herein described, by way of example only, with reference to the accompanying drawings, wherein.

DESCRIPTION OF THE PREFERRED EMBODIMENTS

Figure 1:
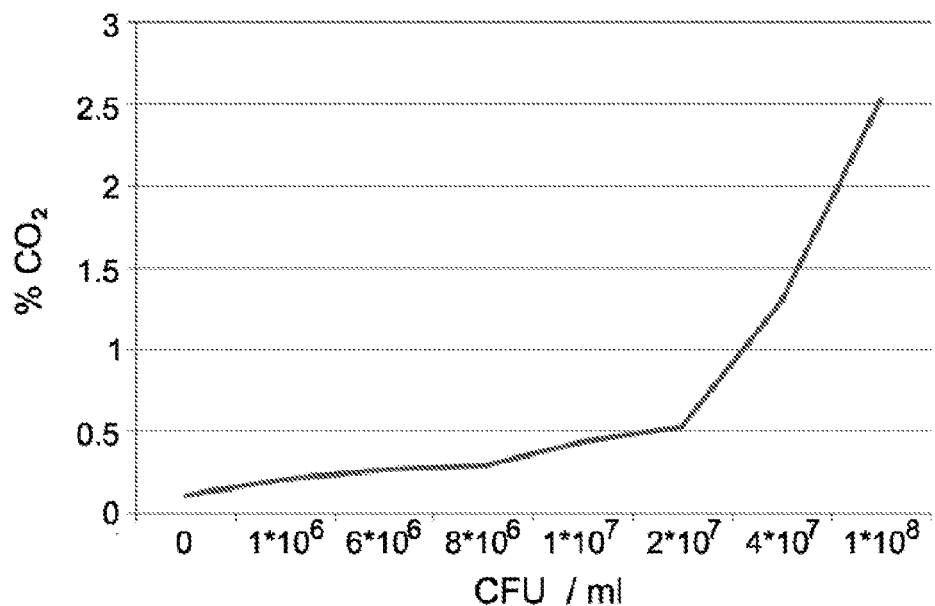
FIG. 1 is a plot of % $CO_2$ vs. bacterial concentration in an experimental platelet unit.

The principles and operation of in-situ real-time and non-invasive detection of microorganisms in biological materials according to the present invention may be better understood with reference to the drawings and the accompanying description.

The present invention is a method and apparatus for in situ detection of microorganisms, in biological materials. The term "in situ" as used herein means that detection is performed directly through the walls of the original storage container without opening or sampling the storage container. The detection is non-invasive and nondestructive in the sense that measurement procedure does not destroy or affect in any way the biological material; thus the biological material can still be used for its original purpose, after the detection procedure. The detection is real-time in the sense that no incubation period is required and the results of the detection can be obtained within a relatively short time period (seconds or minutes).

The detection method can be applied also for quantitative analysis and estimation of a level of biological activity of microorganisms for example in agar plates and monitoring of biological activity such as in the case of measuring bacterial growth in the bacterial production of pharmaceutical proteins. Microorganisms are used commercially to produce foods (such as vinegar, yogurt, cause beer and wine spoilage), antibiotics and chemicals such as ethanol. Production of some of the most important and complex pharmaceuticals such as insulin, hormones and antibodies is carried out using microorganisms (such as *E. coli*) that have been modified genetically using recombinant DNA technology. From the early stages of commercial production of recombinant proteins, the handling of recombinant cultures has been subject to challenges. One of these challenges is how to cope with the problem of instability in recombinant organisms. Commercial production of products on a large scale, especially in the pharmaceutical industry using fermenters, depends heavily on the stable maintenance of the organisms. The fermentation process of recombinant bacteria needs to be precise and the bacteria concentration has to be monitored.

The inventive method is based on measuring the absorption of an infrared beam that is transmitted through a gaseous atmosphere above the biological material. Living microorganisms produce metabolic gases such as carbon dioxide ($CO_2$) during respiration. By means of infrared absorption the concentration of metabolic gases are measured inside the storage container.

The detection apparatus detection preferably includes a tunable monochromatic mid-IR light source, an IR detector and an electronic signal processor that receives the signal from the IR detector. The light source is preferably a tunable quantum cascade laser (QCL). The light source could be also a broadband source equipped with narrow-band mid-IR filters. The light source emits light in a frequency range that overlaps at least one absorption line of a probed metabolic gas. In one preferred embodiment the electronic signal processor is just a lock-in amplifier. Use of the tunable light source instead of the fixed wavelength source allows the determination of metabolic gas concentration within the container without etalon use.

In the present invention, the light from the light source is transmitted through the part of the storage container that is not filled with the biological material, and is measured by means of an IR detector. The container could be ether hermetically sealed and impermeable or gas-permeable. In the latter case, the concentration of metabolic gases inside the container is determined by equilibrium conditions between the rate at which metabolic gases are released within the container and rate of diffusion of metabolic gases through the walls of the container. The walls of the container can be transparent or semi-transparent at the operating frequencies of the light source. In some embodiments, the container is equipped with a small reservoir connected to the main body of the container by means of tubing; in which case the IR absorption measurement is done in the gas-connected reservoir.

The primary intended application of the present invention, but by no means the only contemplated application of the present invention, is to detection of bacterial contamination of platelets.

The risk of bacterial contamination in platelets is estimated to be 1 in 1,500 (S. Ribault et al., cited above), which is one to two orders of magnitude higher than the combined risk of viral infections. The majority of all bacterial-transmitted fatalities occur at the end of platelet shelf life. Therefore, the maxim shelf life of platelet has been decreased from 7 to 5 days after blood donation. Reducing the risks of bacterial contamination of transfusion products, especially platelets, is important for preventing complications during the transfusion procedure and to extend the shelf life of the platelets.

The method of the present invention, as applied to platelets, is a non-contact and non-invasive method for detecting bacterial contamination in platelet plastic bags. The method is based on quantitative analysis of metabolic gases such as $CO_2$ released by bacteria inside the platelet plastic storage bag.

The method is a spectroscopic method that uses a mid-IR light source that emits light at frequencies overlapping with strong absorption lines of $CO_2$ or other metabolic gases. The preferred light sources include monochromatic light sources such as QCL or a gas laser, or a broad spectrum light source equipped with a narrow-band filter. The light from the light source is transmitted through the part of the plastic bag that is above the stored platelets and is measured by means of an IR detector. The concentration of $CO_2$ or other metabolic gas is estimated by measuring light absorption within the plastic bag.

The method allows the detection of different transfusion-relevant contaminating bacterial species. This approach provides on-line measurement of respiratory gases such as $CO_2$ at ambient atmospheric concentrations without the need for any pre-concentration or gas separation. The method is non-invasive since it does not require opening the plastic platelet bag for examination.

This non-invasive bacterial detection method represents a new approach to prevent the transmission of bacterial contamination of platelets. One advantage of the method is that all measurements can be performed in real time, until right up to the time of transfusion and therefore the risk for sample errors is reduced to a minimum and the platelets' storage time is extended.

Unlike conventional methods, the method of the present invention can be used with containers that are either sealed and impermeable or permeable to the metabolic gas(es) being monitored. There are cases in which the container should be gas-permeable, such as in case of platelet storage in gas-permeable bags to maintain $O_2$ tension and to allow metabolic $CO_2$ to escape.

The changes that occur to platelets during storage are an inevitable consequence of the fact that platelets are best preserved under optimal metabolic conditions at 20-24° C. in bags that are permeable to $O_2$ and $CO_2$, with sufficient agitation to permit good oxygenation, to prevent platelet aggregation and to maintain optimal viability and functional properties. Consequently, platelet concentrates contain platelets that after collection fail to survive for more than about 5 days. Those platelet storage conditions promote ongoing bacterial proliferation throughout the storage period and thus increase the risk of transmitted bacteria. In cases of permeable containers, any bacterial growth is reflected in real-time gas concentration changes. In case the bacteria are no longer alive the carbon dioxide concentration, for example, remains at equilibrium with the air outside the storage tank.

The concentration of metabolic gases inside a gas permeable container is determined by equilibrium conditions between the rate of release of metabolic gases and the rate of diffusion of the metabolic gases through the walls of the container.

The equation for gas (such as $CO_2$) production and transport through the walls of a permeable container is:

$$\frac{\partial N_{CO_2}}{\partial t} = -JA + W \tag{1}$$

where $N_{CO_2}$ is the number of $CO_2$ gas molecules, J is the diffusion flux through the walls of the container, A is the surface area of the walls exposed to the gas exchange and W is the source term that describes the total rate of $CO_2$ production inside the container. The diffusion flux is given by $$J = (n_{in} - n_{out})K \tag{2}$$

where the concentration of $CO_2$ inside the container is $n_{in}$, $n_{out}$ is the ambient concentration of $CO_2$ outside the container and K is the membrane permeability coefficient. W for a bacteria-contaminated biological material is given by:

$$W = N_{bact} r_{bact} + W_0 \tag{3}$$

where $N_{bact}$ is the number of bacteria inside the container, $r_{bact}$ is the $CO_2$ emission rate by bacteria in units of $m^3$/sec and $W_0$ is the $CO_2$ emission rate of the biological material. At equilibrium conditions the total $CO_2$ emission rate is equal to the rate of diffusion through the container walls:

$$\frac{\partial N_{CO_2}}{\partial t} = 0$$

and the number of bacteria $N_{bact}$ is related to the concentration of $CO_2$ gas inside the container $n_{in}$ by:

$$N_{bact} = \frac{1}{r_{bact}}((n_{in} - n_{out})KA - W_0) \tag{4}$$

If the biological material contains no bacteria, then $N_{bact} = 0$ and the initial concentration of $CO_2$ gas inside the container is:

$$n_{in0} = n_{out} + W_0/KA \tag{5}$$

Then from Eq. (4) the change of $CO_2$ concentration $\Delta n_{CO2} = n_{in} - n_{in0}$ is related to $N_{bact}$ by:

$$N_{bact} = \frac{\Delta n_{CO2} KA}{r_{bact}} \tag{6}$$

Thus, the number of bacteria is proportional to the change of $CO_2$ concentration $\Delta n_{CO2}$, to the container wall permeability coefficient K and to the container wall surface area A and inversely proportional to the $CO_2$ emission rate by a single bacterium $r_{bact}$. Eq. (6) was derived under an assumption of equilibrium conditions for gas emission and diffusion through the container wall. If the container is sealed, then this equation is inapplicable because then there is no gas exchange through the container walls. In this case the concentration of $CO_2$ is given by Eq. (1) with the first term on the right-hand side equal to zero:

$$\frac{\partial N_{CO_2}}{\partial t} = N_{bact} r_{bact} + W_0 \tag{7}$$

In that case $N_{CO_2}$ increases with time as long as there is biological activity inside the container that is responsible for $CO_2$ emission.

Eq. (6) can be used to detect biological activity in a biological material stored in a gas-permeable container. The procedure is especially simple if the only source of emission of $CO_2$ gas inside the container is bacteria. In that case $W_0 = 0$ and concentration of $CO_2$ gas inside the container is equal to the ambient concentration: $n_{in0} = n_{out}$ as follows from Eq. (5). In that case, an increase of concentration $\Delta n_{CO2}$ above the ambient concentration indicates the presence of biological activity inside the container.

If $W_0 > 0$, then detection of bacterial contamination can be done by measuring the change $\Delta n_{CO2}$ of $CO_2$ concentration relative to a reference concentration associated with uncontaminated biological material.

The change of concentration $\Delta n_{CO2}$ can be measured via IR absorption of an IR beam from a tunable IR light source such as a Quantum Cascade Laser through the container walls. The use of a tunable source instead of a fixed wavelength source allows direct measurement of $CO_2$ concentration inside the container regardless of container material. It is assumed only that the container walls are at least partially transparent in the mid-IR frequency or wavenumber range where strong absorption of $CO_2$ occurs (around 2360 $cm^{-1}$-2390 $cm^{-3}$). Also, it is assumed that the path length of the optical beam in the gaseous atmosphere inside the container is sufficiently long for an accurate measurement of % $CO_2$.

The dependence of % $CO_2$ level on the increase of bacterial contamination was studied experimentally. *Staphylococcus epidermidis* obtained from the American Type Culture Collection (ATCC) were used to contaminate a bag of platelets that were collected from a single donor by apheresis. The bacterially inoculated apheresis platelets were agitated at 22° C. and measurements were performed using QCL spectroscopy. The platelet container was measured before and during bacterial contamination. Samples were taken from the contaminated platelet bag and a standard culture plate count was used for determining bacterial concentration [colony forming unit (CFU)/mL] in the platelet medium.

Referring now to the drawings, FIG. 1 is a plot of % $CO_2$ vs. bacterial concentration. The bacterial concentration that was measured at the point where % $CO_2$ started to rise was between $1*10^6$ CFU/mL to $6*10^6$ CFU/mL. The Y axis shows % $CO_2$ level and the X axis shows bacterial concentration measured using standard titration analysis.

Figure 2A:
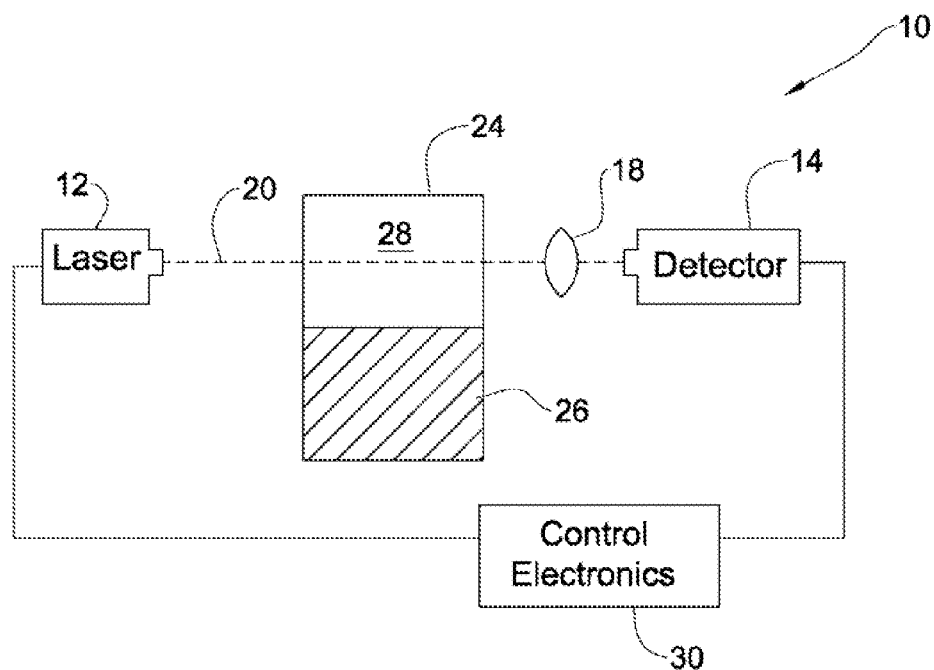
FIGS. 2A, 2B and 3 illustrate systems of the present invention.
Figure 2B:
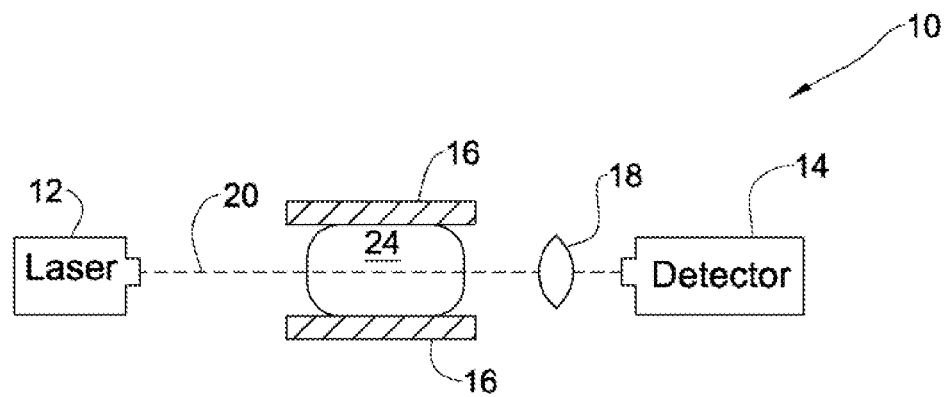

FIGS. 2A and 2B illustrates a system 10 of the present invention for measuring the concentration of carbon dioxide in the dead space 28 above the platelets 26 in a gas-permeable bag 24 that has been removed temporarily from storage and agitation for the purpose of measuring the concentration of carbon dioxide in dead space 28. A tunable infrared laser 12 (for example a QCL) and an infrared detector 14 are positioned so that the light beam 20 from laser 12 is aimed at detector 14. Light beam 20 is focused on detector 14 by a calcium fluoride lens 18. Bag 24 is positioned between laser 12 and detector 14 so that light beam 20 traverses dead space 28. FIG. 2B shows system 10 from above, showing that bag 24 is held in place by two vertical walls 16. FIG. 2A shows system 10 from the side without walls 16. Control electronics 30 tune laser 12 to emit light beam 20 at selected wavelengths in the vicinity of 4.3 microns at a pulse repetition rate of 5 KHz, receive the corresponding response signals from detector 14, and analyze those signals in support of an estimation of the concentration of carbon dioxide in dead space 28. As noted above, the signal reception and analysis portion of control electronics 30 may be as simple as merely a lock-in amplifier that locks onto the 5 KHz signal from receiver 14 and displays the amplitude and phase of that signal. For an accurate measurement of the concentration of carbon dioxide in dead space 28 the path length of light beam 20 across the interior of bag 24 should be at least several centimeters.

Figure 3:
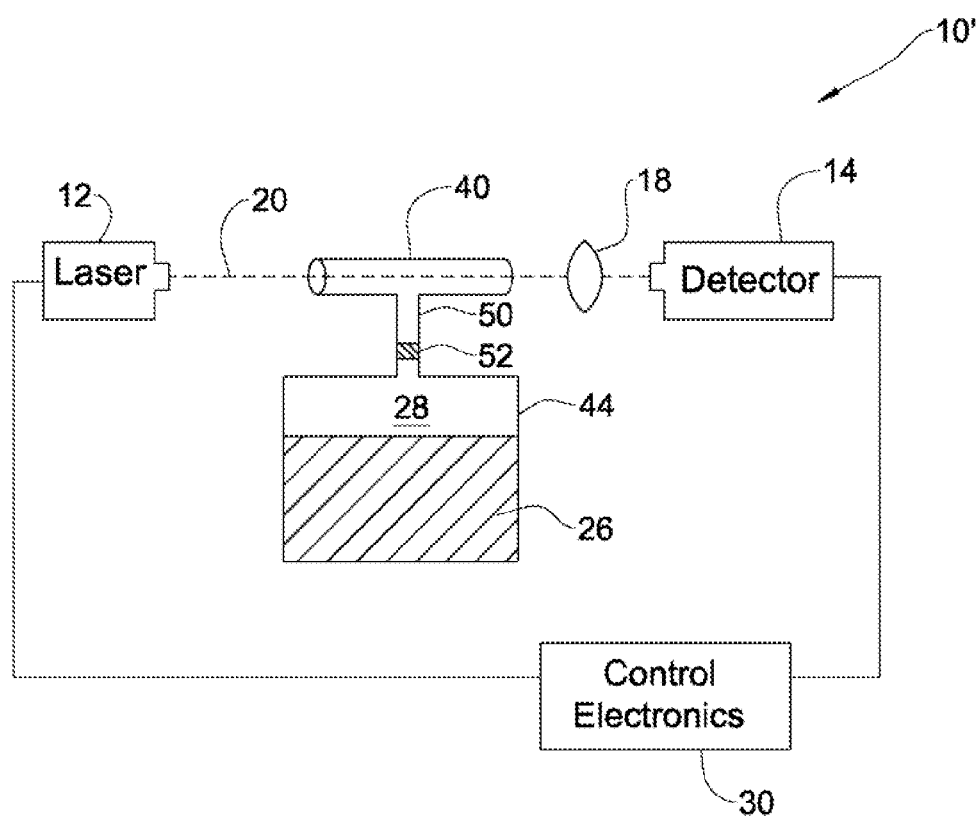

In practice, a sufficiently long optical path through bag 24 may not be available, and/or the walls of bag 24 may not be sufficiently transparent at the relevant wavelengths to allow an accurate measurement of the concentration of carbon dioxide in dead space 28. FIG. 3 illustrates a modified system 10' that deals with these problems. System 10' is identical to system 10, except that bag 24 has been transformed into a modified bag 44 by connecting one end of a plastic tube 50 to bag 24 by fusion with a heating instrument, as is routinely done to platelet bags in blood banks, for various reasons of their own. Such procedures are performed routinely without damaging the platelet bags or introducing contamination. The other end of tube 50 is connected to a rigid, closed, cylindrical reservoir 40 that is transparent at the relevant wavelengths and that is long enough to provide an optical path of several centimeters for light beam 20. A filter 52, in tube 50, that is permeable to gases but not to liquids, keeps liquids from bag 44 out of reservoir 40 but allows the gaseous contents of reservoir 40 to equilibrate with the gaseous contents of dead space 28 so that the concentration of carbon dioxide in reservoir 40 is identical to the concentration of carbon dioxide in dead space 28. The equilibration of the concentration of carbon dioxide between reservoir 40 and dead space 28 occurs sufficiently fast that no special steps need to be taken to hasten this equilibration. Effectively, the interior of reservoir 40 is an extension of dead space 28.

The following framework provides a mathematical description of the measurement procedure of metabolic gas concentration inside a container using a tunable IR light source.

The transmitted laser light intensity $I(\lambda_0)$ measured at the detector at the laser central wavelength $\lambda_0$ is given by:

$$I(\lambda_0) = \eta I_0 \int_{\lambda_{min}}^{\lambda_{max}} f(\lambda - \lambda_0) \exp[-\alpha_\lambda (cl + c_0 l_0)] \qquad (8)$$

where $I_0$ is the laser intensity, $\eta$ is the total intensity loss that is not related to optical gas absorption, $\alpha_\lambda$ is the absorption coefficient (in $cm^{-1}$) at the given wavelength of the light $\lambda$, c is the concentration of the probed gas (by volume) inside the container, $c_0$ is the concentration of the probed gas outside the container in the atmosphere, l is the path length inside the container, $l_0$ is the path length outside the container between the IR source and the IR detector, and $f(\lambda-\lambda_0)$ is the laser spectral distribution function around the central wavelength $\lambda_0$. The integration limits $\lambda_{min}$ and $\lambda_{max}$ with $\lambda_{min} < \lambda_0 < \lambda_{max}$ are assumed to be such that $f(\lambda)$ is nearly zero outside the integration domain.

The absorption coefficient $\alpha_\lambda$ can be calculated as: $\alpha_\lambda = n\sigma(\lambda)$, where $n = P/k_B T$ is the concentration of gas molecules and $\sigma(\lambda)$ is the absorption cross section in $cm^2$.

The signal on the detector is assumed to be proportional to the transmittance intensity. In the case of a tunable laser the central wavelength can be changed within a certain range.

The signal on the detector S can be written as $$S(x, \lambda_i) = b \int_{\lambda_{min}}^{\lambda_{max}} f(\lambda - \lambda_i) \exp[-\alpha_\lambda (x + c_0 l_0)] d\lambda \qquad (9)$$

where x=cl and b is a constant. x (and therefore c) can be found from equation (9) if measurements are done at two or more wavelengths of the light $\lambda_i$. In that case the unknown constant b can be eliminated from the set of equations. An elegant way to find the concentration c from n measured values of the signal $S_i$, i=1, . . . , n, at n different wavelengths $\lambda_i$ is by means of nonlinear minimization with respect to x of the following function s(x)

$$s(x) = \sum_{i=1}^{n-1} \left[ \log\left(\frac{S(x, \lambda_i) + \varepsilon}{\delta(x, \lambda_n)}\right) - \log\left(\frac{S_i + \varepsilon}{S_n}\right) \right]^2 \qquad (10)$$

Where $\varepsilon$ is a noise level at the detector. s(x) is essentially the least square norm of the logarithm of the ratio between measured and theoretical signals at wavelengths $\lambda_i$, i=1, . . . , n−1 and the signal at wavelength $\lambda_n$. The parameter $\varepsilon$ ensures that the function s(x) is not singular if one of the $S_i=0$. From equation (10) the concentration c can be determined, provided that the optical path length l is known.

Example

Carbon Dioxide Absorption Simulations and Evaluation

Figure 4:
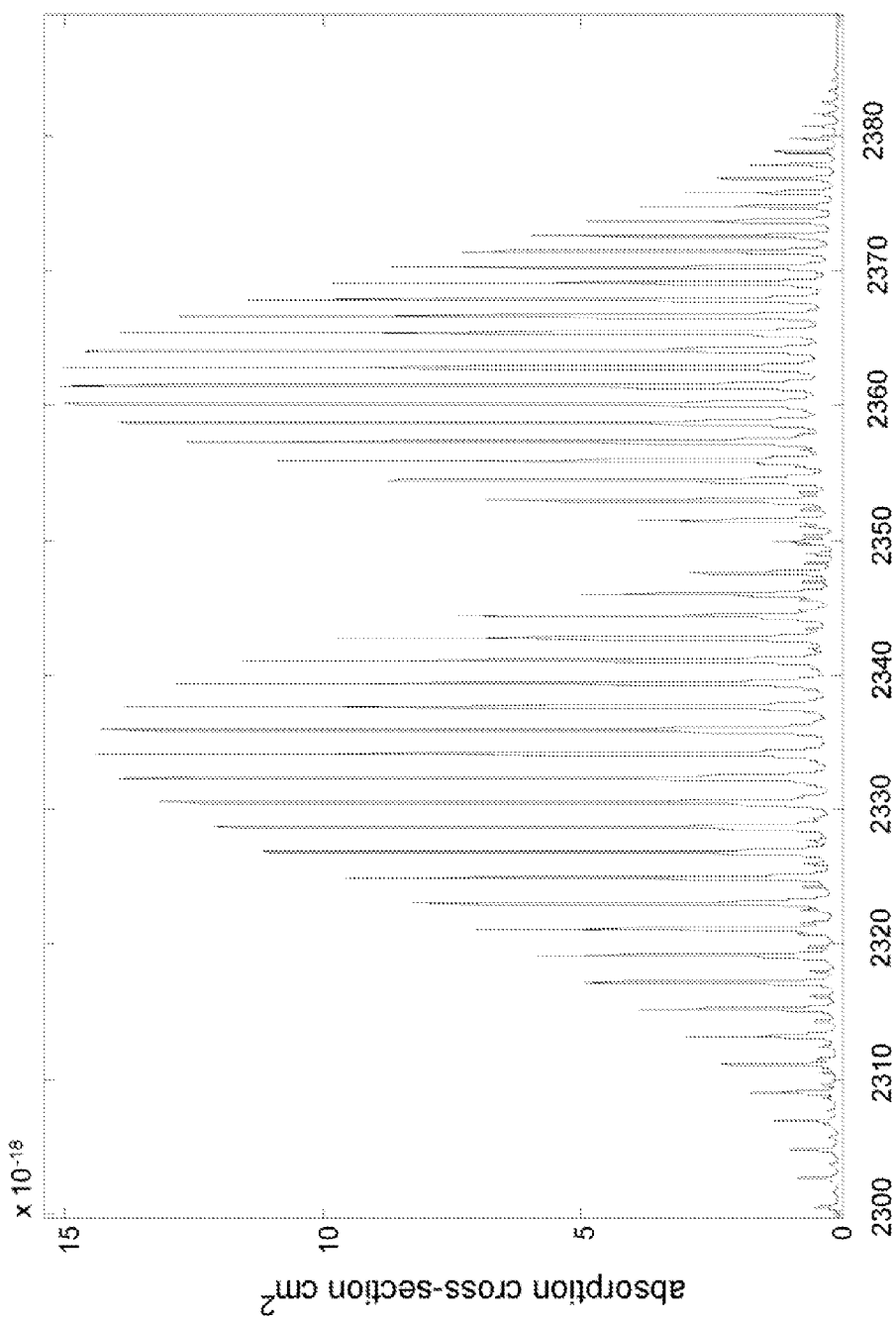
FIG. 4 is a graph of $CO_2$ absorption cross section at ambient conditions.

Simulations of $CO_2$ infrared absorption within plastic bags were performed using $CO_2$ line intensities from the HITRAN database. FIG. 4 is a graph of $CO_2$ absorption cross section at ambient conditions (1 atm, 25° C.).

Figure 5:
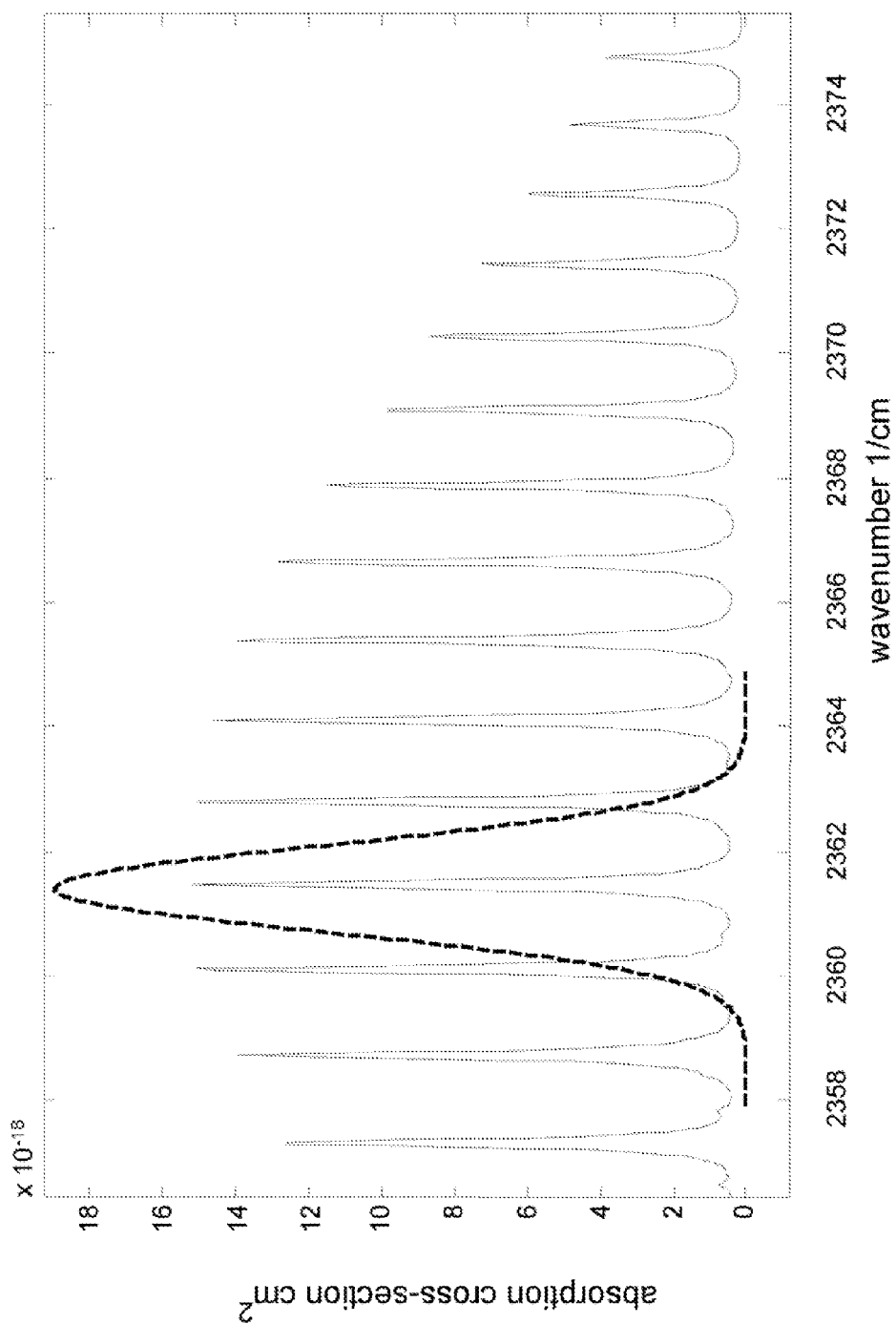
FIG. 5 shows the spectrum of a QCL beam superposed on the $CO_2$ absorption spectrum.

The typical width of a $CO_2$ absorption line is about 0.07 $cm^{-1}$, whereas the width of the $CO_2$ QCL emission is about 1 $cm^{-1}$. FIG. 5 shows the spectrum of the QCL beam tuned to a central wavenumber of 2361.4 $cm^{-1}$ corresponding to the maximum of absorption of the $CO_2$ gas.

Figure 6:
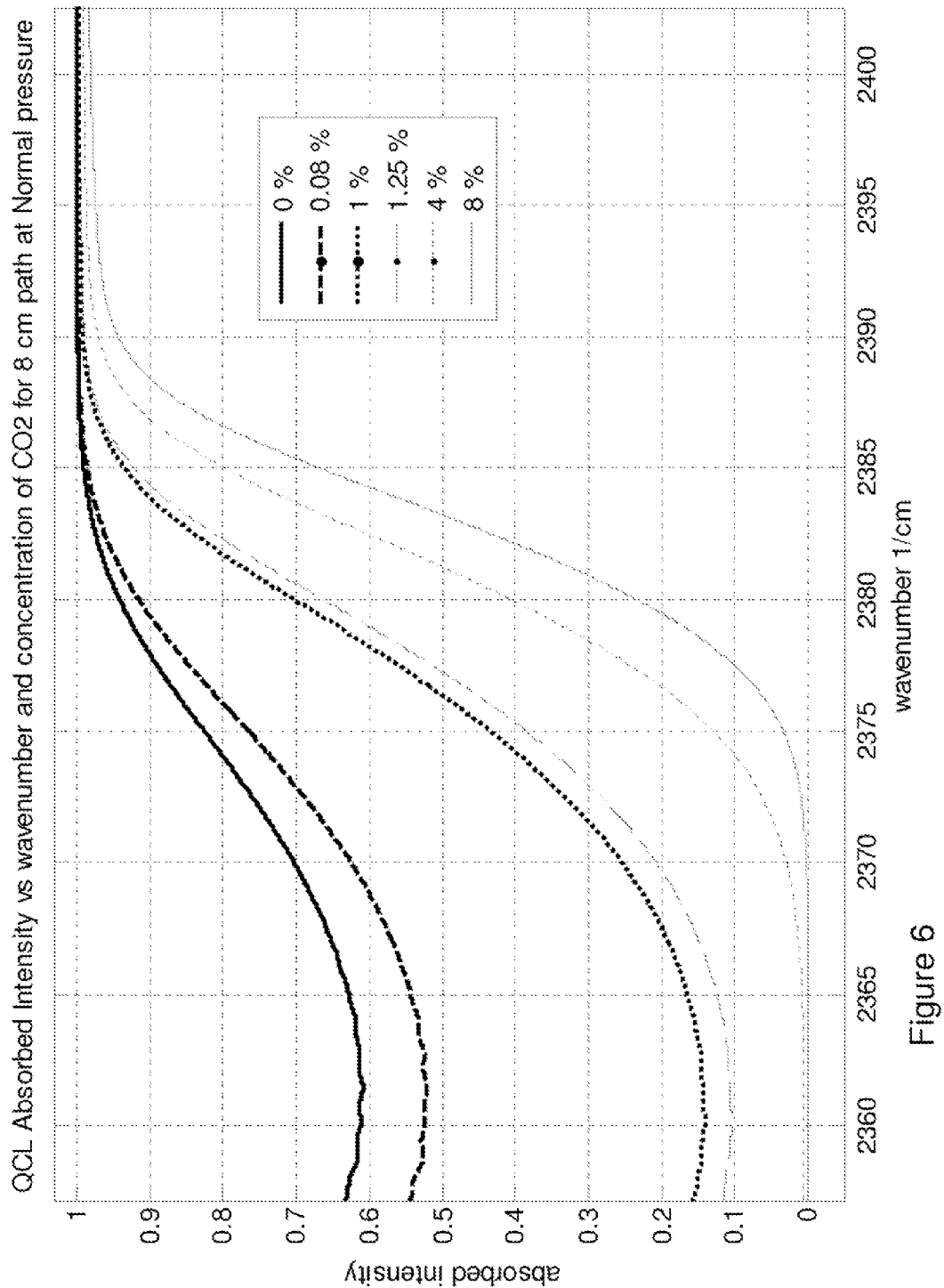
FIG. 6 shows simulated absorption vs. wavenumber at four different $CO_2$ concentrations.

FIG. 6 shows simulated absorption vs wavenumber, at four different $CO_2$ concentrations, of the light beam of a QCL laser calculated using equation (8) in the IR spectral range 2355 $cm^{-1}$-2410 $cm^{-1}$. The graph shows smooth dependence of the spectra on wavenumber and also shows that transmittance increases as the wavenumber changes from 2360 $cm^{-1}$ to 2410 $cm^{-1}$ The preferred apparatus 10 or 10' for detection of metabolic $CO_2$ inside a platelets plastic bag 24 or 44 includes a tunable QCL laser 12, an IR detector 14, a $CaF_2$ plano-convex lens 18, and control electronics 30 whose signal reception and analysis portion is just a lock-in amplifier. QCL laser 12 operates in pulse mode with a repetition frequency of 5 kHz and a pulse width of 500 nsec. The tunability range of QCL laser 12 includes the measurement range from 2361.4 $cm^{-1}$ to 2391 $cm^{-1}$.

The procedure for determination of $CO_2$ concentration within container 44 includes the following steps.

1. Transmitting light beam from QCL laser 12 through reservoir 40 connected to plastic bag container 44 as shown in FIG. 3.

2. Measuring the signal at IR detector 14 at several wavelengths of the light $\lambda_i$, i=1, . . . , n in the wavenumber range from 2361.4 $cm^{-1}$ to 2391 $cm^{-1}$.

3. Estimating the concentration c of $CO_2$ gas inside container 44 using Eq. 10 for the various $\lambda_i$ by means of nonlinear minimization of the function s(x) with respect to x.

Yet another use of the technology is related to the detection of isotopologies of methanolic gases.

Isotopologues are molecules that are identical except for their isotopic composition. Examples of the isotopologues of carbon dioxide are $^{12}C^{16}O_2$, $^{13}C^{16}O_2$, $^{16}O^{12}C^{18}O$, $^{16}O^{13}C^{18}O$. The natural abundance of isotopologues that contain a rare isotope is negligible in comparison to the common molecule. For example, the natural abundance of $^{13}O^{16}O_2$ is 0.0111%, and the natural abundance of $^{18}O^{13}C^{18}O$ is $10^{-8}$. Different isotopologues of the same molecules have different vibrational frequencies, and thus different absorption spectra in the IR region. For example, molecules of $^{13}C^{16}O_2$ have a strong absorption at 2270.29 $cm^{-1}$, while the absorption strength of the nearest absorption line of $^{12}C^{16}O_2$ at 2277.427 $cm^{-1}$ is weaker by a factor of about 30 than that of $^{13}C^{16}O_2$. This provides means for discrimination between different isotopologues of the same molecules by means of infrared absorption spectroscopy. In particular, a typical tunable QCL operating in cw mode can have a beam spectral width as narrow as 0.01 $cm^{-1}$. That provides means for unambiguous measurement of concentrations of isotopologues of a molecule under study in a setup as described above.

Isotopologues can serve as biomarkers to trace particular metabolic processes. One example of such an application is the use of D-glucose-$^{13}C_6$ as a carbon based nutrition source for bacteria for checking specific metabolic processes. That can be used for example to study the efficiency of the fermentation reaction of glucose for ethyl alcohol production at different stages of the fermentation process.

The present invention has been described with respect to its application to blood transfusion materials, such as platelets, red blood cells and plasma, as the biological material. More generally, the present invention is applicable to any biological material, including inter alia sugars, proteins, nucleic acids, and combinations thereof, and living entities such as cells and tissues. The sources of the biological materials may be human, animal, plant, fungal or microbial, and may be produced by biotechnological methods.

With regard to food materials, rapid and simple identification of microorganisms in food products is an essential task for the food industry. Traditional methods such as conventional plating, biochemical tests, and immunological methods have several steps and may take a long time to get confirmatory results. The present invention addresses the need of the food industry for rapid assays of the presence of microorganisms in food products.

Bacterial viability determination is one of the major concerns in the food industry because injurious bacteria cause a significant health threat if they revive during food distribution and storage and it is important to examine the efficacy of various intervention treatments used in food processing. Conventional microbiology methods cannot give an accurate measure of bacterial viability because such methods do not distinguish between live cells and dead cells.

The present invention has been described in terms of its application to the detection of contamination of biological materials by microorganisms. The present invention also is applicable to monitoring biological materials to which microorganisms have been introduced deliberately. Specifically, the present invention may be used to monitor the progress of fermentation.

Micro-organisms are exploited to produce a wide variety of products using fermentation. These include:
Dairy products—Cheese, yogurt
Beverages—Beer, wine
Single Cell Proteins (SCP)
Antibiotics
Chemicals—Citric and acetic acid, amino acids, enzymes, vitamins
Fuels—Ethanol, methanol, methane While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method for in situ real-time non-invasive monitoring of contaminations in a sealed platelet bag, said method including the steps of:
  (a) providing a sealed platelet bag comprising:
    (i) a main body which comprises platelets and a dead space to accommodate a metabolic gas; and optionally
    (ii) a reservoir in fluid communication with said dead space, said reservoir being transparent to an optical wavelength which is absorbed by carbon dioxide;
  (b) providing a detection apparatus comprising:
    (i) a tunable mid-infrared (mid-IR) light source, wherein said mid-IR light source is a quantum cascade laser (QCL);
    (ii) an infrared detector; and
    (iii) an electronic signal processor; and
  (c) determining the concentration of carbon dioxide in the dead space of said sealed platelet bag or in said reservoir in fluid communication with said dead space by:

(i) positioning said sealed platelet bag or said reservoir between the tunable QCL and the infrared detector of said detection apparatus;
(ii) measuring the absorption coefficient of the laser at the IR detector for several wavelengths in the mid-IR spectral range; and
(iii) determining the concentration of carbon dioxide inside said platelet bag without using an etalon and without sampling and/or incubating a sample;

wherein an increase of the concentration of carbon dioxide in said dead space or in said reservoir in fluid communication with said dead space relative to a reference concentration is indicative of a contamination, and wherein determining the concentration of carbon dioxide in step (c)(iii) is made via a nonlinear minimization model $S(x, \lambda i)$ as provided by function $s(x)$ below:

$$s(x) = \sum_{i=1}^{n-1} \left[ \log\left(\frac{S(x, \lambda_i) + \epsilon}{S(x, \lambda_n)}\right) - \log\left(\frac{S_i + \epsilon}{S_n}\right) \right]^2$$

where $\epsilon$ is a noise level at the detector, and $S(x, \lambda i)$ is provided by the following equation:

$$S(x, \lambda_i) = b \int_{\lambda_{min}}^{\lambda_{max}} f(\lambda - \lambda_i) e^{-\alpha_\lambda (x + c_0 l_0)} d\lambda$$

where b is a constant, $f(\lambda - \lambda i)$ is the laser spectral distribution function around the central wavelength $\lambda i$, $\alpha\lambda$, is the absorption coefficient, x=cl wherein c is the gas concentration inside the container, l is the path length inside the container, c0 is the concentration of the probed gas outside the container and l0 is the path length outside the container between the infrared source and the detector.

2. The method of claim 1 wherein the mid-IR spectral range used in step (c)(ii) is 2355 cm$^{-1}$ to 2410 cm$^{-1}$.

3. The method of claim 1 wherein said contamination is a bacterial or a fungal contamination.

* * * * *